US00PP23164P3

(12) United States Plant Patent
Ramon Alvarez Britos

(10) Patent No.: US PP23,164 P3
(45) Date of Patent: Nov. 6, 2012

(54) ***STEVIA* PLANT NAMED 'AKH L1'**

(50) Latin Name: ***Stevia rebaudiana* (Bert.) Bertoni**
Varietal Denomination: AKH L1

(75) Inventor: Edgar Ramon Alvarez Britos, Asunción (PY)

(73) Assignee: PureCircle Sdn Bhd, Bandar Enstek (MY)

( * ) Notice: Subject to any disclaimer, the term of this patent is extended or adjusted under 35 U.S.C. 154(b) by 4 days.

(21) Appl. No.: 13/068,857

(22) Filed: Jan. 18, 2011

(65) Prior Publication Data

US 2012/0090062 P1 Apr. 12, 2012

Related U.S. Application Data

(60) Provisional application No. 61/336,506, filed on Jan. 22, 2010.

(51) Int. Cl.
*A01H 5/00* (2006.01)

(52) U.S. Cl. ..... Plt./226

(58) Field of Classification Search ..... Plt./373, Plt./263.1, 226, 258
See application file for complete search history.

*Primary Examiner* — Howard Locker
(74) *Attorney, Agent, or Firm* — Ballew Law

(57) ABSTRACT

A new and distinct cultivar of *stevia* plant named 'AKH L1', characterized by its combination of late harvest cycle, light green or yellow green leaves, high number of nodes on the main stem, high Rebaudioside A of total Glycoside Steviol content, and high yielding of dried leaves at harvest.

5 Drawing Sheets

Genus and species: *Stevia rebaudiana* (Bert.) Bertoni.
Variety denomination: 'AKH L1'.

STATEMENT REGARDING FEDERALLY SPONSORED RESEARCH OR DEVELOPMENT

None

BACKGROUND AND SUMMARY OF THE INVENTION

The present invention relates to a new and distinct variety of *stevia* (*Stevia rebaudiana* (Bert.) Bertoni), which has been given the variety denomination of 'AKH L1'.

The new *stevia* plant cultivar is a selection resulting from a controlled breeding program of *stevia* plants at Guayaibi, San Pedro, Paraguay in 2006 through the controlled pollination of seed parent 'EIRETE' (unpatented) and pollen parent 'AKH/EM1' (unpatented). The new cultivar was selected as a single plant within a population of plants resulting from this controlled pollination of *stevia* plants in 2006 at an experimental station at Guayaibi, San Pedro, Paraguay. Selection criteria was a combination of Rebaudioside A content equal to more than 50% of total steviol glycols, high yield of leaves per hectare, and resistance to leaf spot diseases. 91.5% of the Total Glycoside Steviols are present in the leaves of the claimed variety, with the remaining 8.5% of the Total Glycoside Steviols present in the stems and branches of the claimed variety. The selection was subsequently evaluated for a number of years at the Experimental Station at Guayaibi, San Pedro, Paraguay.

Asexual reproduction of the new cultivar by cutting propagation since 2007 at Guayaibi, San Pedro, Paraguay in field nurseries has demonstrated that the new cultivar reproduces true to type with all of the characteristics, as herein described, firmly fixed and retained through successive generations of such asexual propagation.

The new variety can be compared to the seed parent 'Eirete'. In Guayaibi, San Pedro, Paraguay the plant height of 'AKH L1' is classified as 'medium size' (51-70 cm) whereas the plant height of 'Eirete' is classified as 'high size' (80 cm). The harvest cycle of 'AKH L1' is 'late' whereas the harvest cycle of 'Eirete' is 'medium'. In Guayaibi, San Pedro, Paraguay the leaf color of 'AKH L1' is 'light green or yellow green' whereas the leaf color of 'Eirete' is 'dark green'. The percentage of Rebaudioside A of total Glycoside Steviol of 'AKH L1' is 89% whereas the percentage of Rebaudioside A of total Glycoside Steviol of 'Eriete' is 52%. Table 1 provides further comparisons of the distinguishing characteristics for the claimed variety and both the seed and pollen parents.

SUMMARY OF THE INVENTION

The following characteristics of the new cultivar have been repeatedly observed and can be used to distinguish 'AKH L1' as a new and distinct cultivar of a *stevia* plant:

1. late harvest cycle
2. light green or yellow green leaf
3. many nodes on main stem
4. medium number of basal buds
5. Stevioside content 1.3%
6. Rebaudioside A content 11.5%
7. total of Esteviosido+Rebaudioside A 12.8%
8. 89% of Rebaoudiosido A of total Glycoside Steviol
9. yields 4,500 kg/ha of dried leaves in three cuts

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'AKH L1'.

DETAILED BOTANICAL DESCRIPTION

Figure 1:
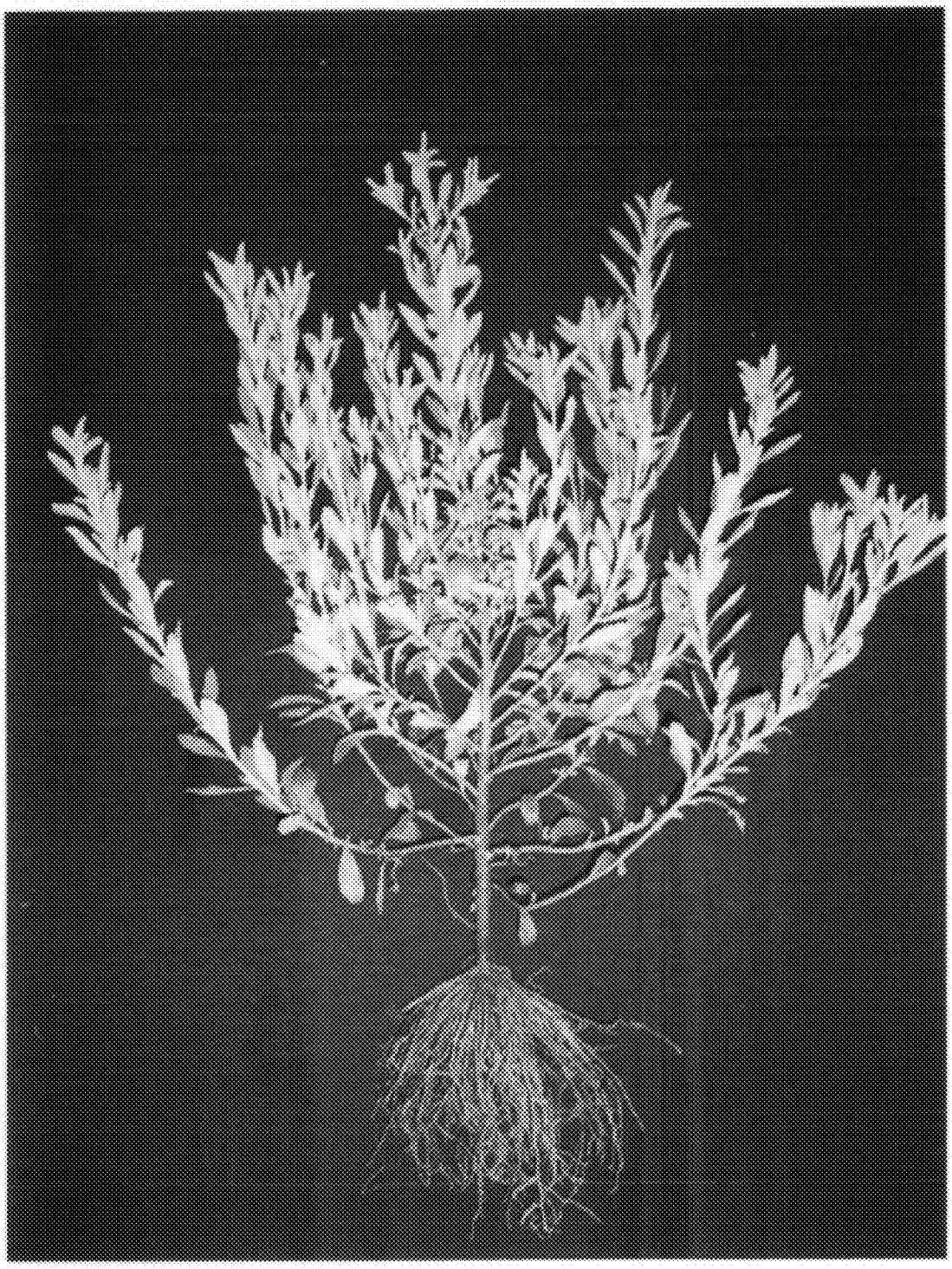
FIG. 1 illustrates an 'AKH L1' plant from roots to top of the plant.
Figure 2:
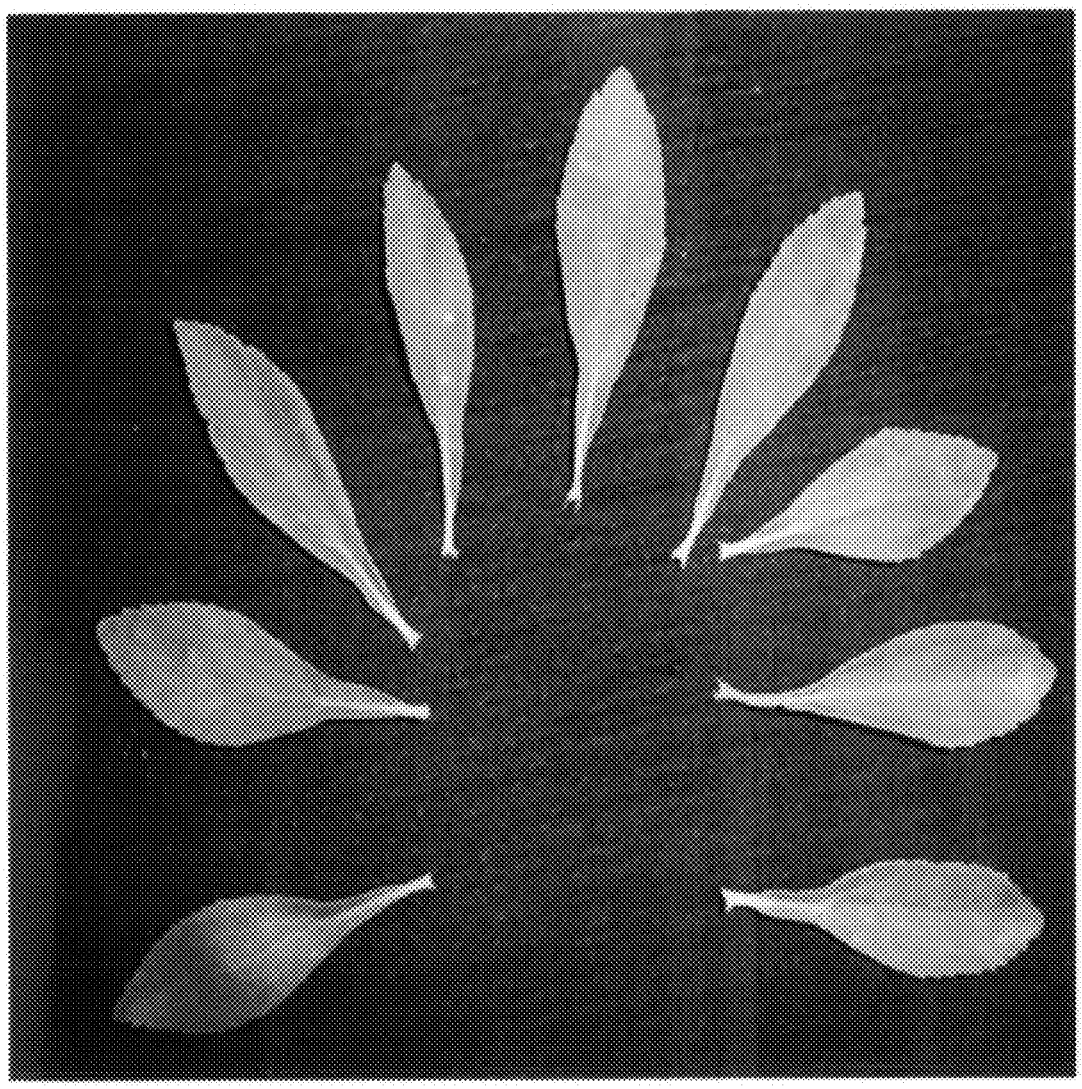
FIG. 2 illustrates 'AKH L1' leaves.
Figure 3:
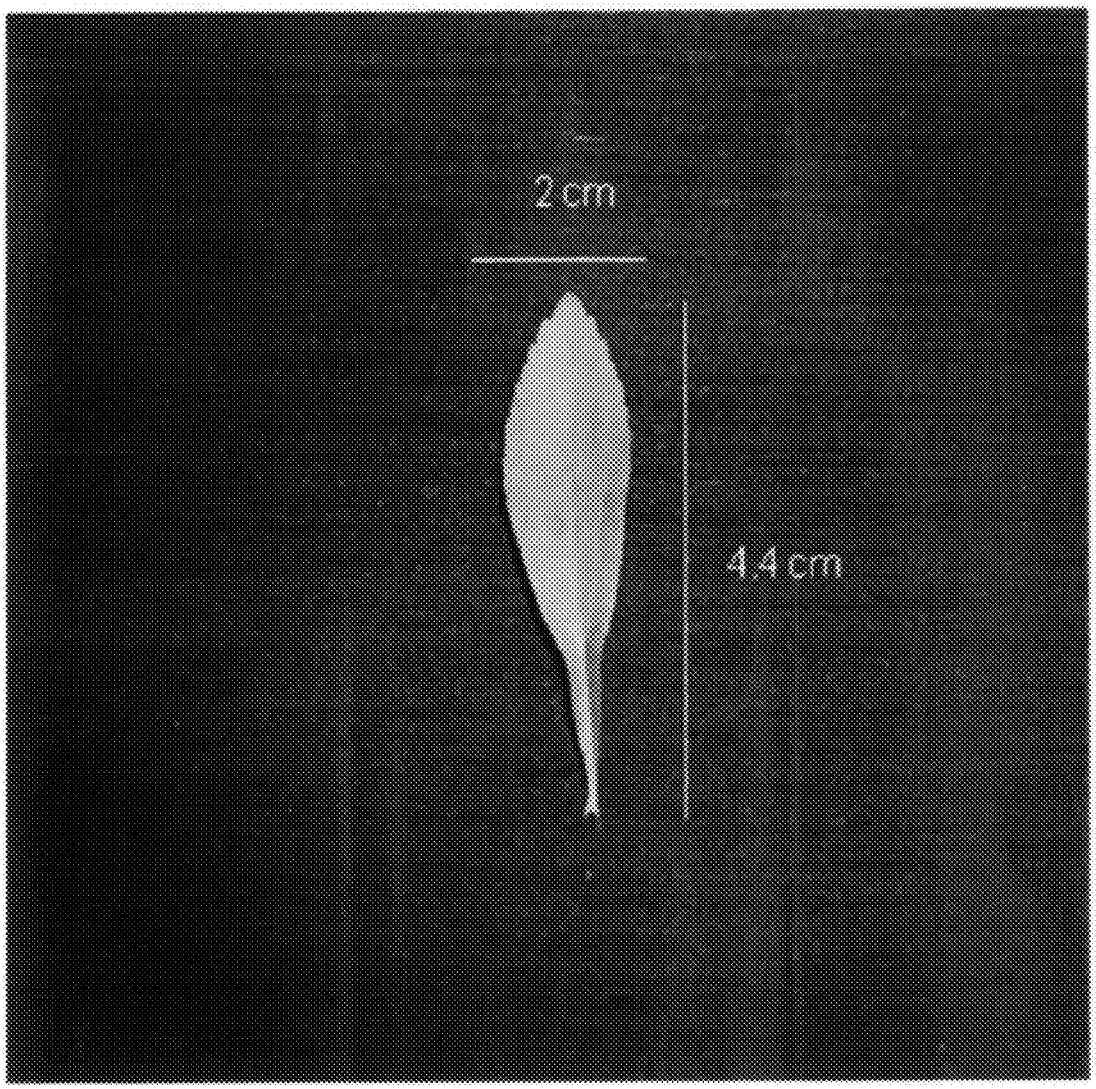
FIG. 3 illustrates an 'AKH L1' leaf, including the shape and dimensions.
Figure 4:
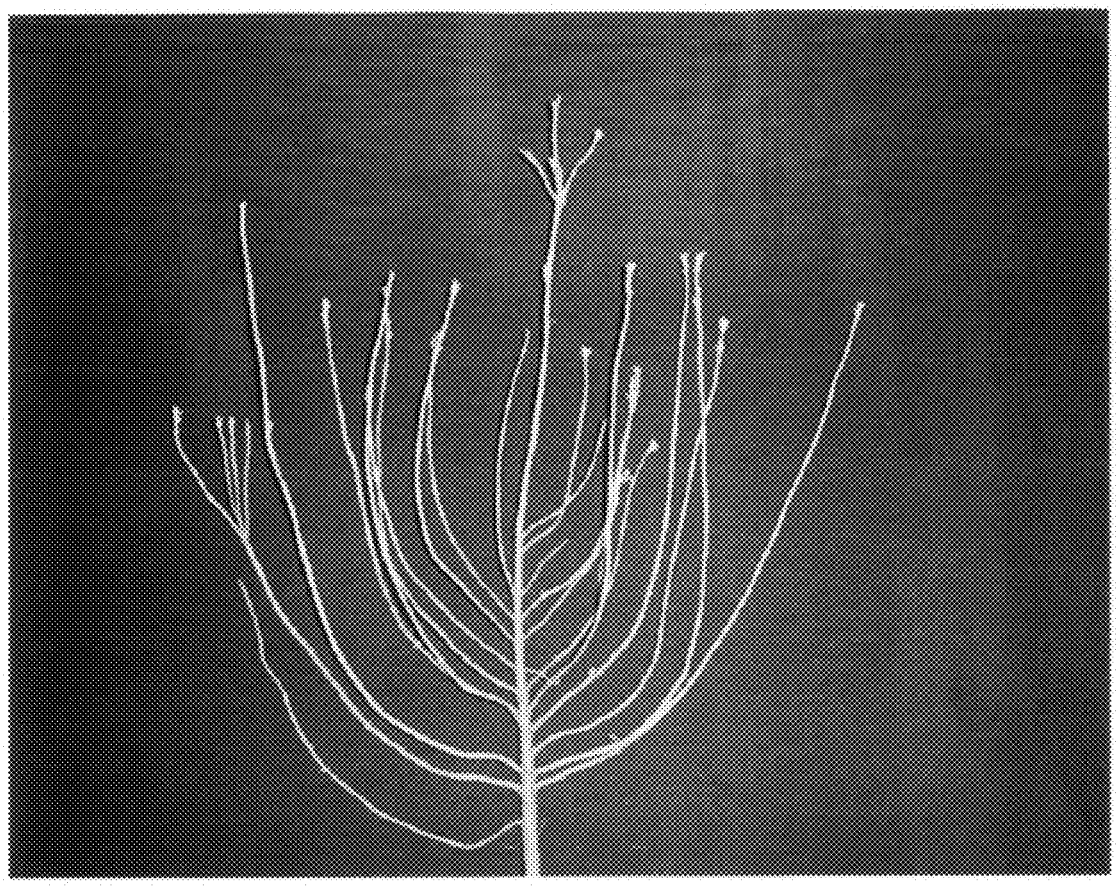
FIG. 4 illustrates the branches, without leaves, of an 'AKH L1' plant.
Figure 5:
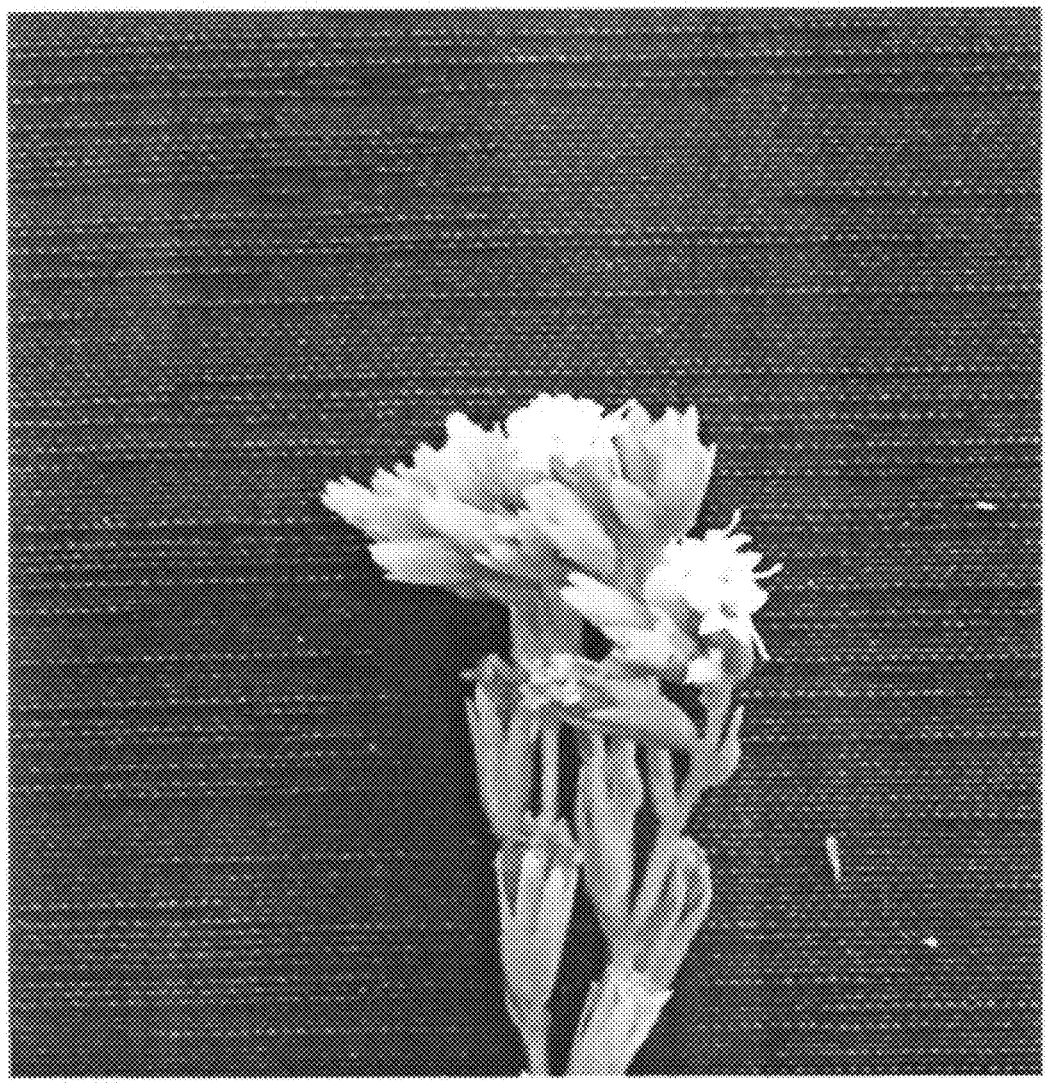
FIG. 5 illustrates the flowers of an 'AKH L1' plant.

The following is a detailed botanical description of a new and distinct variety of a *stevia* plant known as 'AKH L1'. Plant observations were made on plants grown in Guayaibi, San Pedro, Paraguay. Unless indicated otherwise, the descriptions disclosed herein are based upon observations made in February 2008 of mature 'AKH L1' plants (age 6 months) grown in outdoor field plantings with day temperature ranging from 25° C. to 35° C., night temperatures ranging from 22° C. to 30° C., and light levels ranging from 20 to 25 klux. 'AKH L1' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light quality, light intensity, day length, cultural conditions and the like. Color notations are based on The Royal Horticultural Society Colour Chart, of The Royal Horticultural Society, London, 2007 edition.

Botanical classification: *Stevia rebaudiana* (Bert.) Bertoni cultivar 'AKH L1'.

Parentage:

*Parents*.—Seed parent 'Eirete' (unpatented); pollen parent 'AKH/EM1' (unpatented).

Plant:

*Type*.—Shrubby Perennial.

*Growth habit*.—Erect; Main stem with dominance of axillary buds and a good development of lateral branches from the axillary buds.

*Height*.—51 cm to 70 cm.

*Number of nodes on main stem*.—31 nodes.

*Number of basal buds*.—6 to 10 basal buds per plant.

*Harvest cycle*.—Late.

Leaves:

*Length*.—4.4 cm.

*Width*.—2.0 cm.

*Shape*.—Lanceolate.

*New foliage*.—Green RHS 142A.

*Mature foliage*.—Green RHS 141C.

*Upper surface mature foliage*.—Green RHS 141C.

*Lower surface mature foliage*.—Green RHS 141D.

*Veins*.—Green RHS 141D.

*Young shoots*.—Green RHS 142B.

*Mature shoots*.—Yellow-Green RHS 144C.

*Leaf edge*.—Moderately sawn or scalloped.

*Stevioside content*.—1.3%.

*Rebaudioside A content*.—11.5% % of Rebaudioside A of total Glycoside Steviol: 89%.

*Total of stevioside and rebaudioside a*.—12.8%.

Flowers:

*Petals*.—White RHS 155B.

*Sepals*.—Green RHS N144B.

*Bloom period*.—Bloom dates (calculated from planting date): Start of Blooming 120 days; Full bloom — 135 days; End of Blooming 150 days.

*Pedicel length*.—3-4 mm.

*Peduncle length*.—2-4 mm.

*Petiole length*.—2-3 mm.

*Number of flowers per capitulum*.—Five.

*Productivity*.—Yielding of dried leaves in three cuts 4,5000 kg/ha.

*Cold hardiness*.—Cold tolerance from −2° C.

*Heat tolerance*.—Heat tolerance to 40° C.

*Pathogen resistance*.—Moderately resistant to *Septoria steviae*.

*Leaf harvest period*.—Three harvests per year; October, January, and March in Guayaibi, San Pedro, Paraguay.

TABLE 1

Comparison with parents

| | AKH L1 | Eirete (Seed Parent) | AKH EM 1 (Pollen Parent) |
|---|---|---|---|
| Plant: height | 51 cm-70 cm | 80 cm | 30 cm-50 cm |
| Leaf: color | light green/yellow green | dark green | medium green |
| Leaf: shape | lanceolate | lanceolate | oval lanceolate |
| Leaf: edge | moderately sawn or scalloped | strongly sawn or notched | strongly sawn or notched |
| Stevioside content: | 1.3% | 10.4% | 2.1% |
| Rebandioside A content: | 11.5% | 11.3% | 9.2% |
| Number of basal buds | 6-10 buds per plant | 6-10 buds per plant | 6-10 buds per plant |

What is claimed is:

1. A new and distinct cultivar of *stevia* plant named 'AKH L1', substantially as herein shown and described.

* * * * *